(12) United States Patent
Shreve et al.

(10) Patent No.: US 9,546,986 B2
(45) Date of Patent: Jan. 17, 2017

(54) COLUMN MANAGER WITH A MULTI-ZONE THERMAL SYSTEM FOR USE IN LIQUID CHROMATOGRAPHY

(75) Inventors: Joshua A. Shreve, Franklin, MA (US); John Maillet, Hudson, MA (US); Maria Maillet, legal representative, Hudson, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 325 days.

(21) Appl. No.: 14/232,681

(22) PCT Filed: Aug. 16, 2012

(86) PCT No.: PCT/US2012/051088
§ 371 (c)(1),
(2), (4) Date: Jan. 14, 2014

(87) PCT Pub. No.: WO2013/028450
PCT Pub. Date: Feb. 28, 2013

(65) Prior Publication Data
US 2014/0150536 A1    Jun. 5, 2014

Related U.S. Application Data (60) Provisional application No. 61/525,253, filed on Aug. 19, 2011.

(51) Int. Cl.
*G01N 30/30*    (2006.01)
*G01N 30/54*    (2006.01)
(Continued)

(52) U.S. Cl.
CPC .............. *G01N 30/30* (2013.01); *G01N 30/54* (2013.01); *G01N 30/466* (2013.01);
(Continued)

(58) Field of Classification Search
None
See application file for complete search history.

(56) References Cited

U.S. PATENT DOCUMENTS

| | | | |
|---|---|---|---|
| 4,534,941 A * | 8/1985 | Stephens ................ | G01N 30/30 422/109 |
| 5,135,549 A | 8/1992 | Phillips et al. | |

(Continued)

FOREIGN PATENT DOCUMENTS

| | | |
|---|---|---|
| JP | S62261059 | 11/1987 |
| JP | 2007523351 | 8/2007 |

(Continued)

OTHER PUBLICATIONS

International Search Report & Written Opinion in related international patent application No. PCT/US12/51088, mailed on Nov. 8, 2012; 7 pages.

(Continued)

*Primary Examiner* — Paul West
*Assistant Examiner* — Mark A Shabman
(74) *Attorney, Agent, or Firm* — Schmeiser, Olsen & Watts LLP (57) ABSTRACT

A thermal system for use in a column manager of a liquid chromatography system comprises a plurality of spatially separated individually controlled thermoelectric chips. A column module houses a plurality of thermally conductive troughs. Each trough resides in a separate thermal zone to be thermally conditioned individually by one of the individually controlled thermoelectric chips. Each trough is adapted to hold one or more liquid chromatography columns therein. A plurality of spatially separated thermal bridges includes a first thermal bridge thermally coupling one of the thermoelectric chips to a first one of the plurality of troughs and a second thermal bridge of the plurality of thermal bridges (Continued)

thermally coupling another of the thermoelectric chips to a second one of the plurality of troughs.

21 Claims, 10 Drawing Sheets

(51) Int. Cl.
  *G01N 30/60* (2006.01)
  *G01N 30/46* (2006.01)
  *G01N 30/02* (2006.01)
  *G01N 30/88* (2006.01)

(52) U.S. Cl.
  CPC ... *G01N 30/6047* (2013.01); *G01N 2030/027* (2013.01); *G01N 2030/303* (2013.01); *G01N 2030/8881* (2013.01)

(56) References Cited

U.S. PATENT DOCUMENTS

| | | | |
|---|---|---|---|
| 5,238,557 A | | 8/1993 | Schneider et al. |
| 5,641,400 A | | 6/1997 | Kaltenbach et al. |
| 5,958,227 A | * | 9/1999 | Uematsu ............ G01N 30/468 210/198.2 |
| 5,983,710 A | * | 11/1999 | Uhen ................... G01N 30/30 73/23.25 |
| 6,103,081 A | | 8/2000 | Morris et al. |
| 6,355,165 B1 | | 3/2002 | Sutton et al. |
| 6,666,074 B2 | | 12/2003 | Gerner et al. |
| 6,838,640 B2 | | 1/2005 | Wise et al. |
| 7,440,684 B2 | | 10/2008 | Spaid et al. |
| 7,530,259 B2 | | 5/2009 | Tai et al. |
| 2003/0165941 A1 | | 9/2003 | Gjerde et al. |
| 2007/0141593 A1 | | 6/2007 | Lee et al. |
| 2008/0274511 A1 | | 11/2008 | Tan et al. |
| 2008/0302423 A1 | | 12/2008 | Gerhardt et al. |
| 2009/0173146 A1 | | 7/2009 | Pursch et al. |
| 2009/0321356 A1 | | 12/2009 | Gerhardt et al. |

FOREIGN PATENT DOCUMENTS

| | | |
|---|---|---|
| JP | 2008509401 | 3/2008 |
| WO | 0167080 | 9/2001 |
| WO | 2011085337 | 7/2011 |
| WO | 2011085359 | 7/2011 |

OTHER PUBLICATIONS

International Preliminary Report on Patentability in counterpart international patent application No. PCT/US12/51088, mailed on Mar. 6, 2014; 6 pages.
Extended European Search Report in related European Patent Application No. 12825371.3, mailed on Feb. 27, 2015; 7 pages.
Notice of Rejection in counterpart Japanese Patent Application No. 2014-526203, mailed on Apr. 26, 2016; 5 pages.

* cited by examiner

COLUMN MANAGER WITH A MULTI-ZONE THERMAL SYSTEM FOR USE IN LIQUID CHROMATOGRAPHY

RELATED APPLICATION

This application claims priority to and the benefit of U.S. Provisional Application Ser. No. 61/525,253, filed Aug. 19, 2011, titled "Column Manager with a Multi-zone Thermal System for use in Liquid Chromatography," the entirety of which application is incorporated by reference herein.

FIELD OF THE INVENTION

The invention relates generally to liquid chromatography systems. More specifically, the invention relates to a multi-zone thermal system used in liquid chromatography systems to produce a thermal environment for liquid chromatography columns

BACKGROUND

Chromatography is a set of techniques for separating a mixture into its constituents. Generally, in a liquid chromatography analysis, a pump system takes in and delivers a mixture of liquid solvents (and/or other fluids) to a sample manager, where a sample awaits injection into the solvents. The sample is the material under analysis. Examples of samples include complex mixtures of proteins, protein precursors, protein fragments, reaction products, and other compounds, to list but a few. In an isocratic chromatography application, the composition of the liquid solvents remains unchanged, whereas in a gradient chromatography application, the solvent composition varies over time. The mobile phase, comprised of a sample dissolved in a mixture of solvents (and/or other fluids), moves to a point of use, such as a column, referred to as the stationary phase.

By passing the mobile phase through the column, the various components in the sample separate from each other at different rates and thus elute from the column at different times. A detector receives the separated components from the column and produces an output from which the identity and quantity of the analytes may be determined. Temperature can influence the results of the analysis, affecting such properties as the separation performance of the column and the viscosity of a mobile phase. Therefore, maintaining an accurate constant column temperature is important to the accuracy and reproducibility of the results.

SUMMARY

In one aspect, the invention features a thermal system for use in a column manager of a liquid chromatography system. The thermal system comprises a plurality of spatially separated individually controlled thermoelectric chips. A column module houses a plurality of thermally conductive troughs. Each trough resides in a separate thermal zone to be thermally conditioned individually by one of the individually controlled thermoelectric chips. Each trough is adapted to hold one or more liquid chromatography columns therein. A plurality of spatially separated thermal bridges includes a first thermal bridge thermally coupling one of the thermoelectric chips to a first one of the plurality of troughs and a second thermal bridge of the plurality of thermal bridges thermally coupling another of the thermoelectric chips to a second one of the plurality of troughs.

In another aspect, the invention features a liquid chromatography system, comprising a column manager receiving a solvent composition to be delivered to a liquid chromatography column The column manager includes a thermal system providing a multi-zone thermal environment for a plurality of liquid chromatography columns. The thermal system comprises a plurality of spatially separated individually controlled thermoelectric chips. A column module houses a plurality of thermally conductive troughs. Each trough resides in a separate thermal zone to be thermally conditioned individually by one of the individually controlled thermoelectric chips. Each trough is adapted to hold one or more liquid chromatography columns therein. A plurality of spatially separated thermal bridges includes a first thermal bridge thermally coupling one of the thermoelectric chips to a first one of the plurality of troughs and a second thermal bridge of the plurality of thermal bridges thermally coupling another of the thermoelectric chips to a second one of the plurality of troughs.

In still another aspect, the invention features a method for providing a multi-zone thermal environment for liquid chromatography columns. Each thermoelectric chip of a plurality of spatially separated thermoelectric chips is individually controlled. One or more liquid chromatography columns are installed within each compartment of a plurality of adjacent thermally isolated compartments of a column module. One of the thermoelectric chips is physically and thermally coupled to a first one of the plurality of compartments and another of the thermoelectric chips is physically and thermally coupled to a second one of the plurality of compartments. Each compartment is thermally conditioned independently of each other compartment in response to individually controlling the thermoelectric chip thermally coupled to that compartment.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

FIG. 8 is a front view of the column manager with the column module absent to show the thermal bridges coupled to the heatsink a.

DETAILED DESCRIPTION

Systems described herein include a column manager for providing multi-zone independently controlled thermal environments for one or more columns during liquid chromatography analyses, as described herein. Temperature control of the column and of the liquid flowing into the column is an important contributor to producing consistent and reliable results. Various embodiments of these systems relate to liquid-chromatography apparatus, for example, HPLC (High Performance Liquid Chromatography) and UPLC (Ultra Performance Liquid Chromatography) systems.

In brief overview, a column manager includes a column module with a thermal system that provides a multi-zone thermal environment for liquid chromatography columns. The column module has a plurality of compartments, each compartment being capable of holding one or two columns. Each compartment is also an individually controlled thermal zone, each thermal zone being an isolated thermal environment for the one or two columns in that compartment.

The engine for thermally conditioning the thermal zones includes separate individually controlled thermoelectric chips, one thermoelectric chip for each thermal zone. The operation of a thermoelectric chip can either heat or cool a given thermal zone. Thermal bridges thermally couple the thermoelectric chips to the compartments, each thermal bridge coupling a different thermoelectric chip to a different compartment.

The thermoelectric chips share an external heatsink, and a fan moves ambient air over the heatsink. Internal and external thermostats monitor the temperature and can cause power to be cut to the thermoelectric chips should excessive temperatures be detected. Although described herein with reference to two separate individually controlled thermal zones, the principles scale to more than two thermal zones, each such thermal zone being thermally conditioned by an individually controlled thermoelectric chip and coupled thereto by a separate thermal bridge. The use of terms herein, such as front, back, rear, behind, top, bottom, side, left, right, upper, lower, horizontal and vertical, are for simplifying the description of these principles and are not intended as limitations.

Figure 1:
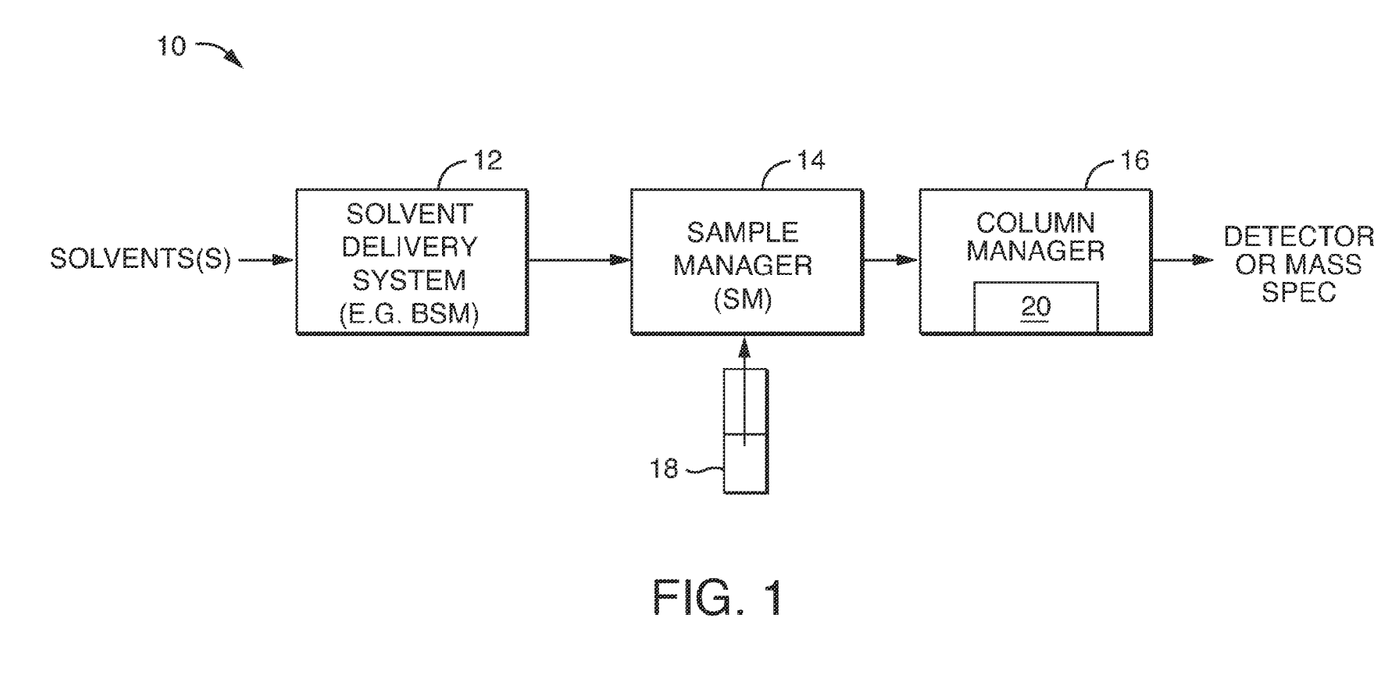
FIG. 1 is a functional block diagram of an embodiment of a liquid chromatography system having a column manager with a thermal system for providing a multi-zone thermal environment for the columns installed within the column manager.

FIG. 1 shows an embodiment of a liquid chromatography system 10 for separating a sample into its constituents. The liquid chromatography system 10 includes a solvent delivery system 12 in fluidic communication with a sample manager 14. Generally, the solvent delivery system 12 includes a pump (not shown) in fluidic communication with solvent reservoirs from which the pump draws solvents. The solvent delivery system 12 delivers a mixture of solvents to the sample manager 14. The sample manager 14 is in fluidic communication with a sample source 18 from which the sample manager acquires and introduces a sample to the solvent composition arriving from the solvent delivery system 12.

In fluidic communication with the sample manager 14 is a column manager 16 for receiving therefrom the solvent composition containing the sample. The column manager 16 holds liquid chromatography columns for use in separating solvent compositions and includes a thermal system 20 with multiple individually controlled thermal zones for these columns, as described herein. In one embodiment, the temperature range for each thermal zone is 4 to 90° C. The thermal zones can be driven to opposite extremes; for example, one thermal zone can be driven to 4° C. while the other thermal zone is driven to 90° C. This practice may be done to precondition a column for the next run. From the column manager 16, the elution passes to a detector, for example, a mass spectrometer, for analyzing the separation. In one embodiment, the solvent delivery system 12, sample manager 14, column manager 16, and detector are separate instruments that can be integrated into a single unit, such as, for example, the ACQUITY UPLC system available from Waters Corporation of Milford Mass.

Figure 2:
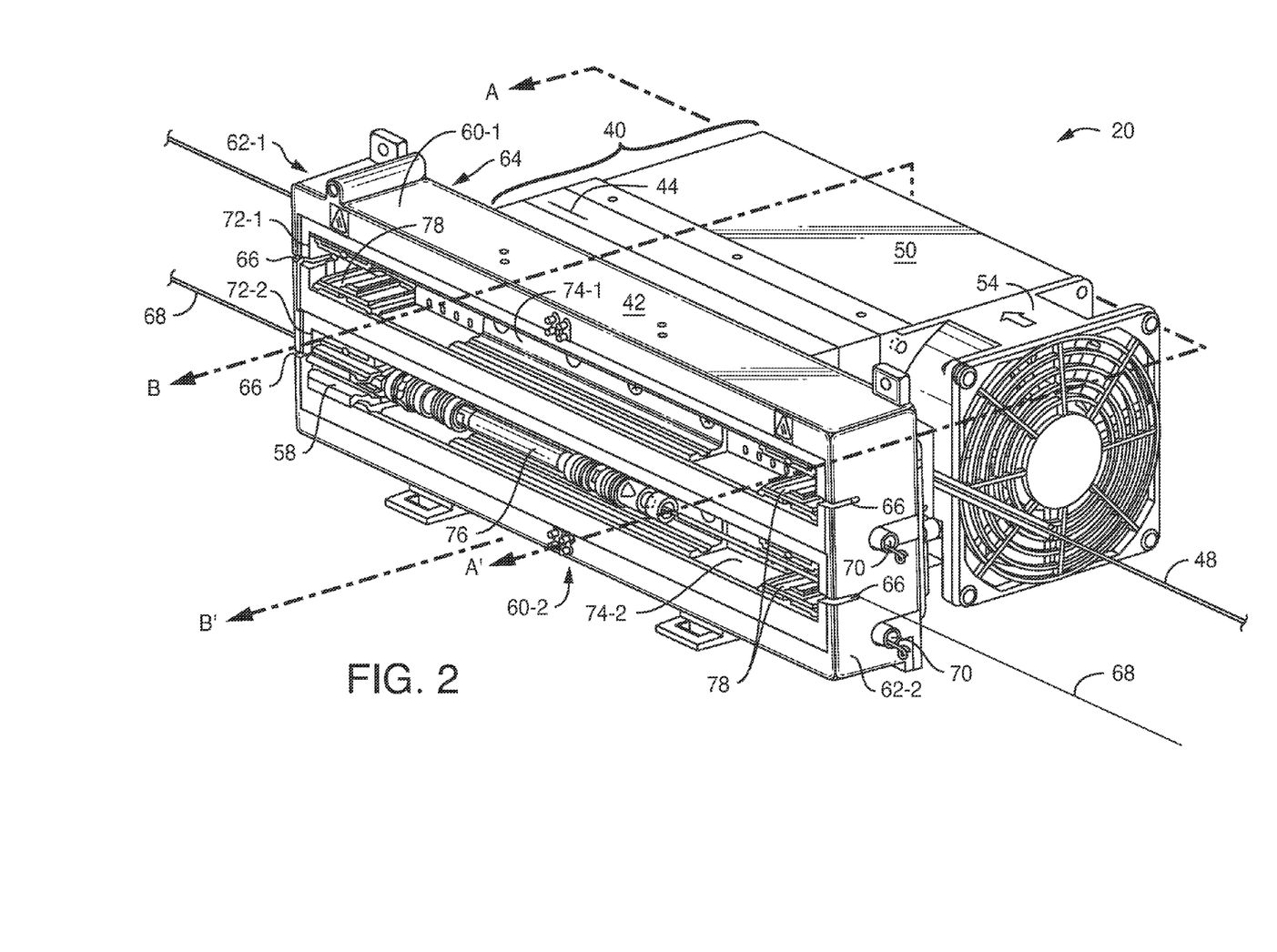
FIG. 2 is a front view of an embodiment of the thermal system of the column manager, including a column module with a plurality of compartments.

FIG. 2 shows an embodiment of the thermal system 20 of the column manager 16. The thermal system 20 includes a heater-cooler module 40 physically and thermally coupled to a column module 42. The heater-cooler module 40 includes an internal side (within the thermal environment) and an external side (outside of the thermal environment). The internal side includes a plurality of spatially separated, individually controlled thermoelectric chips (FIG. 9) embedded in insulation 44. The insulation 44 surrounds each chip on its sides and thermally isolates each chip from each other. The external side of the heater-cooler module 40 includes a bonded fin heatsink 50 physically and thermally coupled to the thermoelectric chips to transfer heat therefrom and a fan 54 for moving air (either blown or drawn) between the fins of the heatsink 50. Electrical signal conductors 48 carry the electrical signals that control operation of the fan 54.

In one embodiment, the thermoelectric chips are Peltier devices, which use electrical power to produce a temperature difference between opposite sides of the device by operating as heat pumps that transfer heat from one side to the other. The temperature difference produced depends on several variables: material properties of the thermoelectric chips, the amount of heat being removed from the cold side, the average temperature of the chambers, and the drive current/voltage. The power of the heater-cooler module 40 is proportional to the size of the thermoelectric chips. In one embodiment, each thermoelectric chip is 4 cm×4 cm×4 mm.

Figure 8:
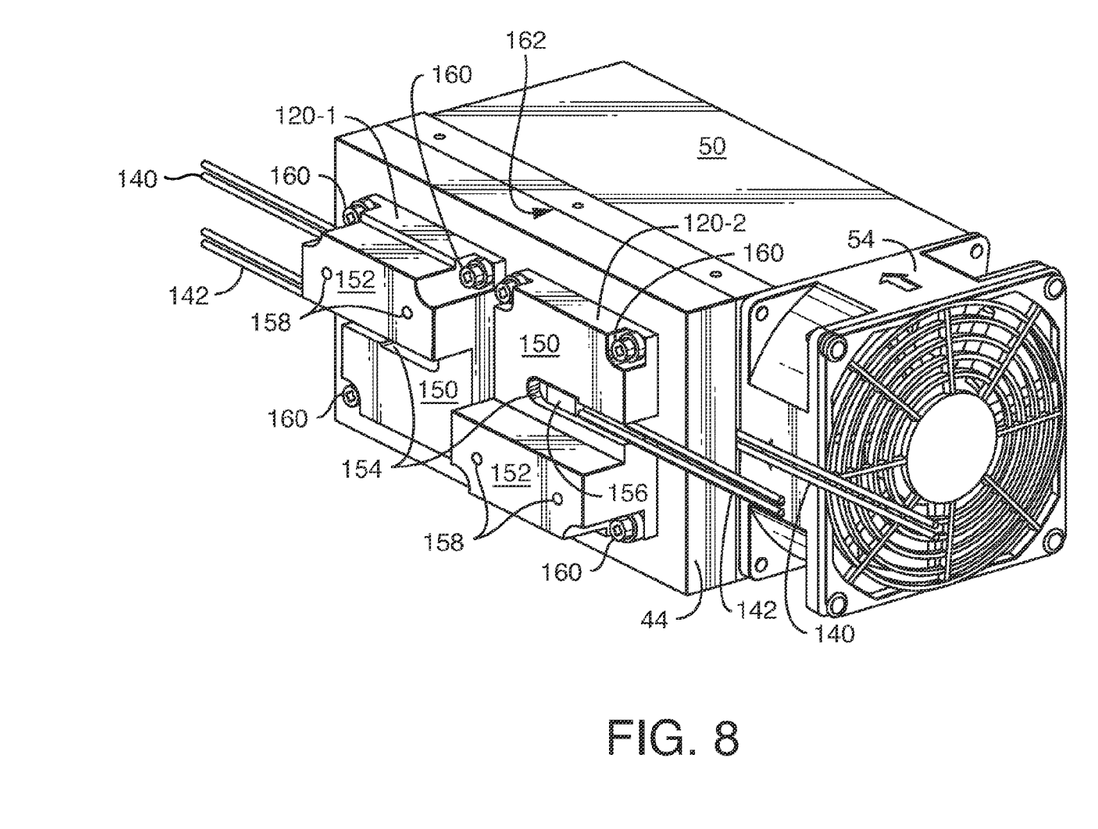

The column module 42 is a generally rectangular housing having sidewalls 60-1, 60-2 (generally, 60), end walls 62-1, 62-2 (generally, 62), a back wall 64, and a front panel (FIG. 8). Slits 66 in the end walls 62 accommodate the passage of microfluidic tubing 68, which convey fluid to and from the columns installed within the column module 42. In one embodiment, the column module 42 is approximately 12 inches in width, approximately 4 inches in height, and approximately 2.25 inches in depth. Behind the column module 42 are a pair of thermal bridges (not shown), one for each thermoelectric chip, for thermally coupling that thermoelectric chip to the column module 42, as described in more detail below.

The column module 42 houses an adjacent pair of horizontally stacked elongated compartments 72-1, 72-2 (generally 72). Each compartment 72 includes a trough 74; the upper compartment 72-1 has the trough 74-1 (referred to as the upper trough) and the lower compartment 72-2 has the trough 74-2 (referred to as the lower trough). Within their respective compartments, the troughs 74 are thermally isolated from each other, with each trough occupying a separate, individually controlled thermal zone. From a lower end of each compartment 72 extends a drain 70, which passes through an opening in the end wall 62-2.

Each trough 74 can hold either one or two chromatography columns. These chromatography columns can have lengths ranging between 5 and 15 cm. Both ends of each trough 74 have a socket 78 adapted to receive a pre-heater assembly. A pre-heater assembly operates to preheat liquid before the liquid passes to a column disposed within that trough.

For example, in FIG. 2, the lower trough 74-2 has a single HPLC column 76 installed within, whereas the upper trough 74-1 is unused. Although an HPLC column 76 is shown in FIG. 2, other embodiments designed for UPLC systems use UPLC columns with shorter lengths and narrower inner dimensions than do their HPLC counterparts. The column 76 is disposed toward the end wall 62-1 of the trough 74-2. Tubing 68 enters the lower trough 74-2 through the slit 66 in the end wall 62-1 and couples to a pre-heater assembly 58. The pre-heater assembly 58 is coupled to one end of the column 76 and provides a fluidic path by which liquid coming from the tubing 68 is heated before passing into the column 76. Tubing 68 is coupled to other end of the column 76 and exits the lower trough 74-2 through the lower slit 66 in the end wall 62-2. Downstream of the column 76, the socket 78 near the end wall 62-1 does not have an installed pre-heater assembly. For configurations in which a trough has two installed columns, arranged end to end, each socket 78 in the trough may have an installed pre-heater assembly to heat the liquid before it enters a respective column Tubing connected to the downstream ends of such columns can exit the trough through the rear of the column module 42.

Figure 3:
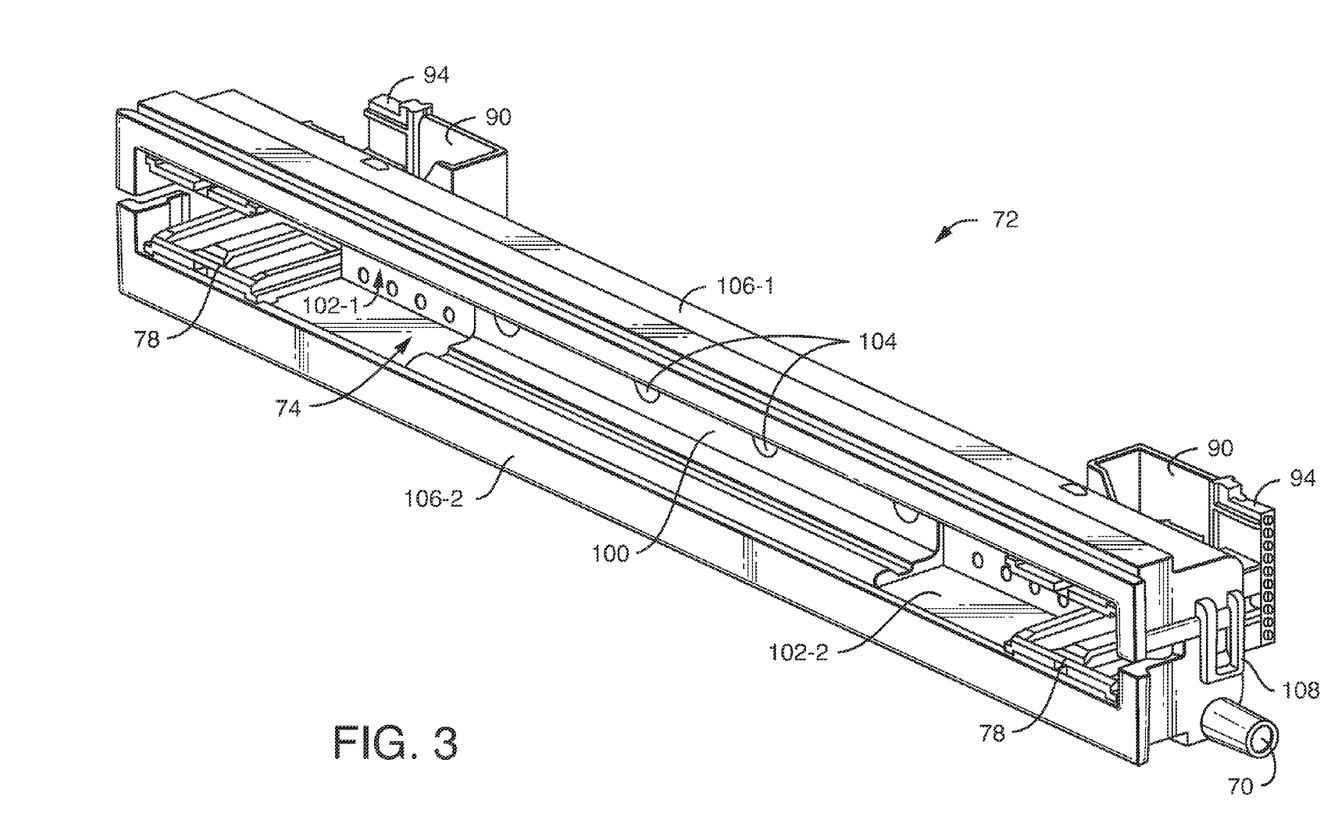
FIG. 3 is a front view of an embodiment of a compartment within the column module.

FIG. 3 shows one embodiment of each compartment 72 of FIG. 2, including the trough 74 (without any columns) and pre-heater sockets 78 at the opposite ends of the trough. To the rear of each pre-heater socket 78 is a ribbon cable 90 electrically connecting that pre-heater socket to an electrical connector 94. The trough 74 has a back surface 100 and opposing side surfaces 102-1, 102-2 (generally, 102). (A front panel (FIG. 9) provides a fourth side for enclosing the trough compartment 72 and providing a tight thermal seal around the trough 74.) The surfaces 100, 102 are made of material of high thermal conductivity (e.g., aluminum) for distributing heat along the trough's length. In addition, the back surface 100 has a plurality of holes 104 for receiving fasteners that connect the trough to a thermal bridge 120 (FIG. 8). Only a subset of the holes 104 is used, those holes used depending upon which thermal bridge the trough is connected to.

An outer shell surrounds the trough 74 and heater sockets 78 on three sides and serves as a drip tray to capture any leakage from the column and tubing or any condensation resulting from cooling the thermal zone. The outer shell is made of two plastic pieces (106-1, 106-2) held together by a resilient snap 108 at each end (the snap at the left of the trough is hidden from view). The snaps 108 reside on one piece of the outer shell and hook over a catch disposed at the edge of the other piece of the outer shell. Other similar snaps holding the shell pieces 106-1, 106-2 together can be on the back of the outer shell. The lower piece 106-2 of the outer shell has the drain 70 for channeling liquid outside of the compartment 72.

Figure 4:
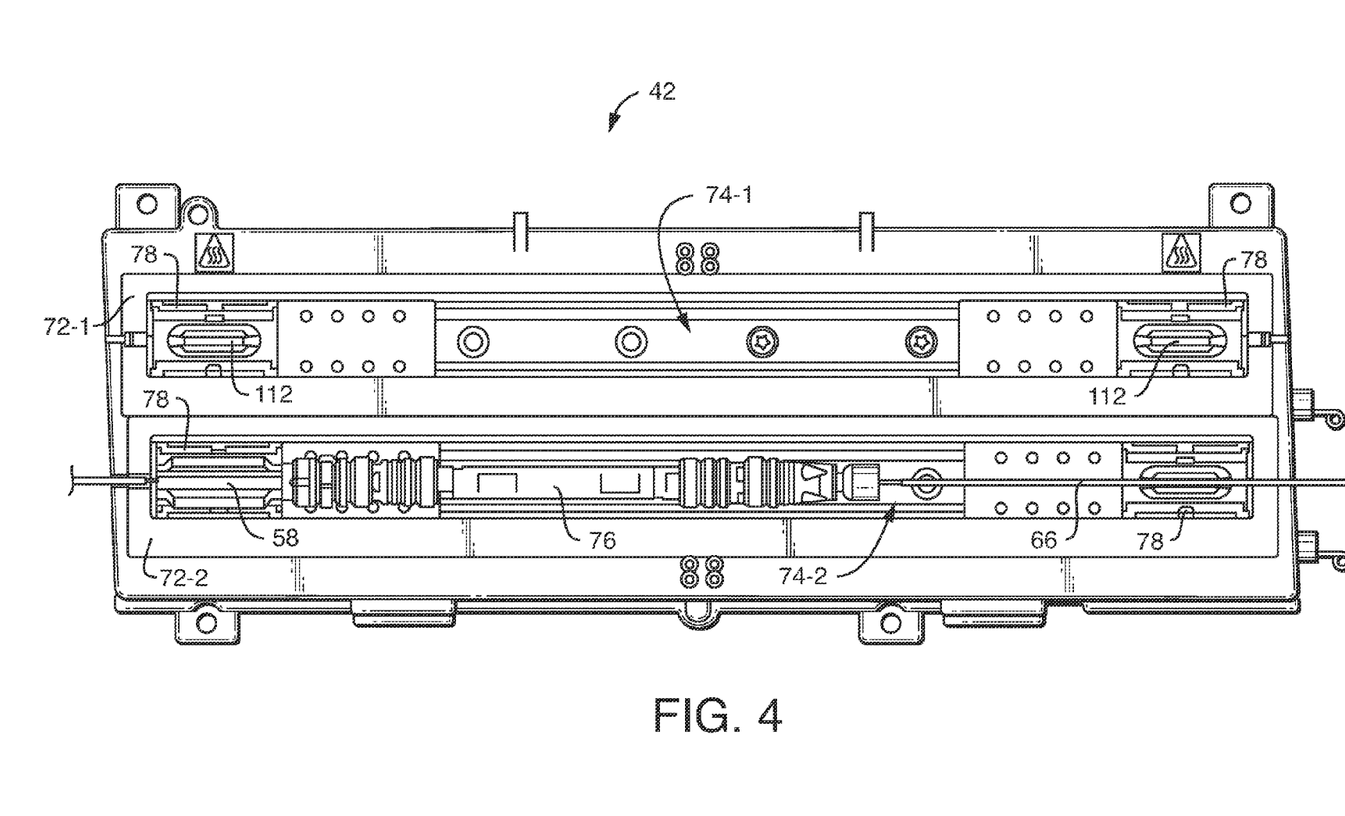
FIG. 4 is a front view of an embodiment of the column module with one empty compartment and one compartment populated with a column and pre heater.

FIG. 4 shows a front view of the column module 42 with the lower trough 74-2 having an installed column 76 and the upper trough 74-1 being unused. In addition, the left-side pre-heater socket 78 of the lower compartment 72-2 has an installed pre-heater assembly 58, whereas the pre-heater sockets 78 of the upper compartment 72-1 and the right-side pre-heater socket 78 of the lower compartment 72-2 are empty. In the empty pre-heater sockets 78 can be seen electrical contacts 112 for connecting and providing power to any installed pre-heater assembly (microfluidic tubing 68 obscures the electrical contacts in the right-side pre-heater socket 78 of the lower compartment 72-2). Ribbon cables 90 (FIG. 3) provide electrical communication between the electrical contacts 112 and an electrical connector 94 (FIG. 3).

Figure 5:
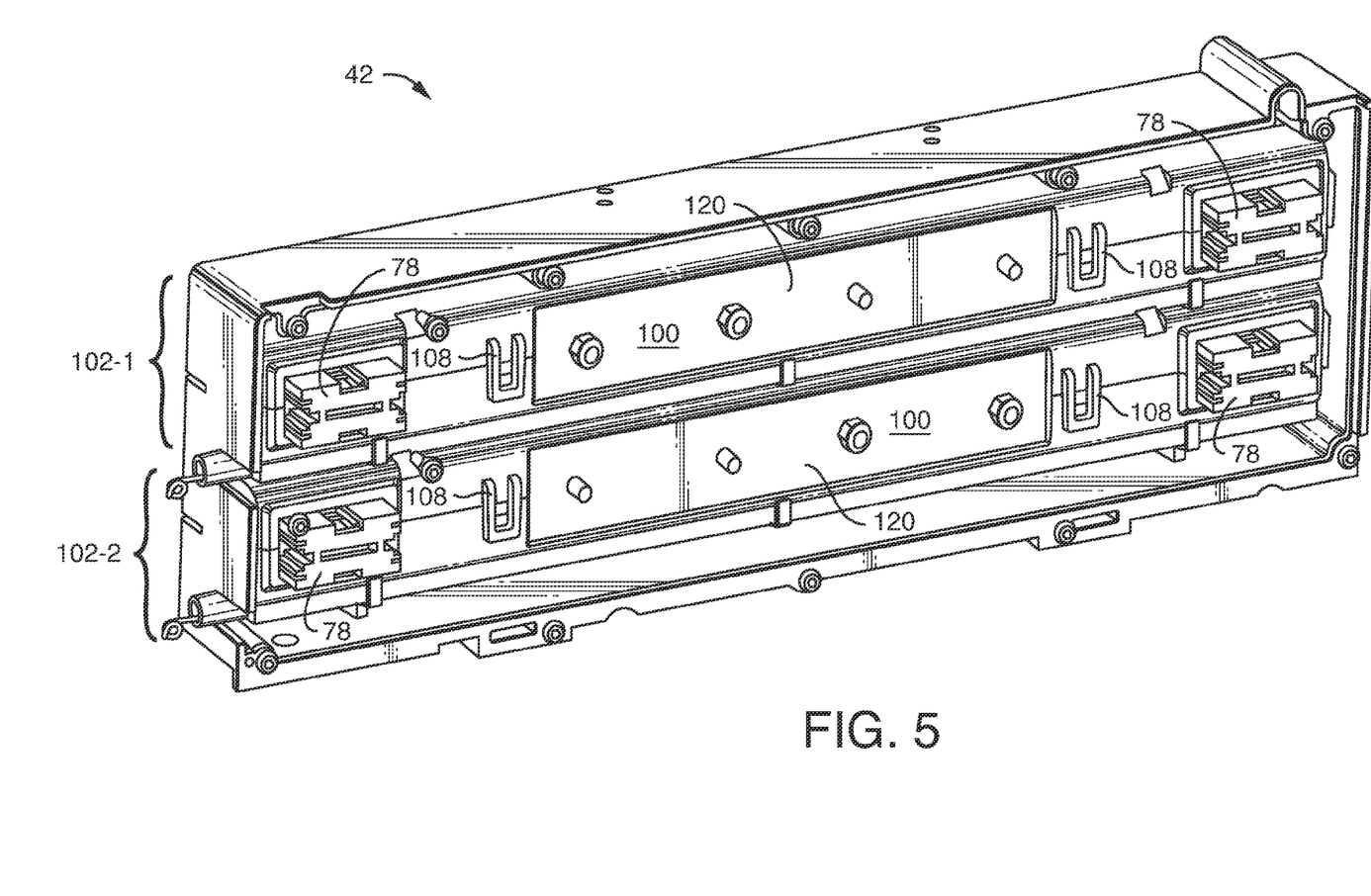
FIG. 5 is a rear view of the column module (absent its back panel) showing the back side of the compartments.

FIG. 5 shows a rear view of the column module 42 without a back panel to reveal the back of the compartments 72-1, 72-2. Snaps 108 on the back join the two halves of each outer shell 106-1, 106-2 (FIG. 3). The joined halves produce an aperture 120 through which the reverse side of the back surface 100 of each trough 74 (FIG. 3) is exposed. Also shown are the reverse sides of the pre-heater sockets 78.

Figure 6:
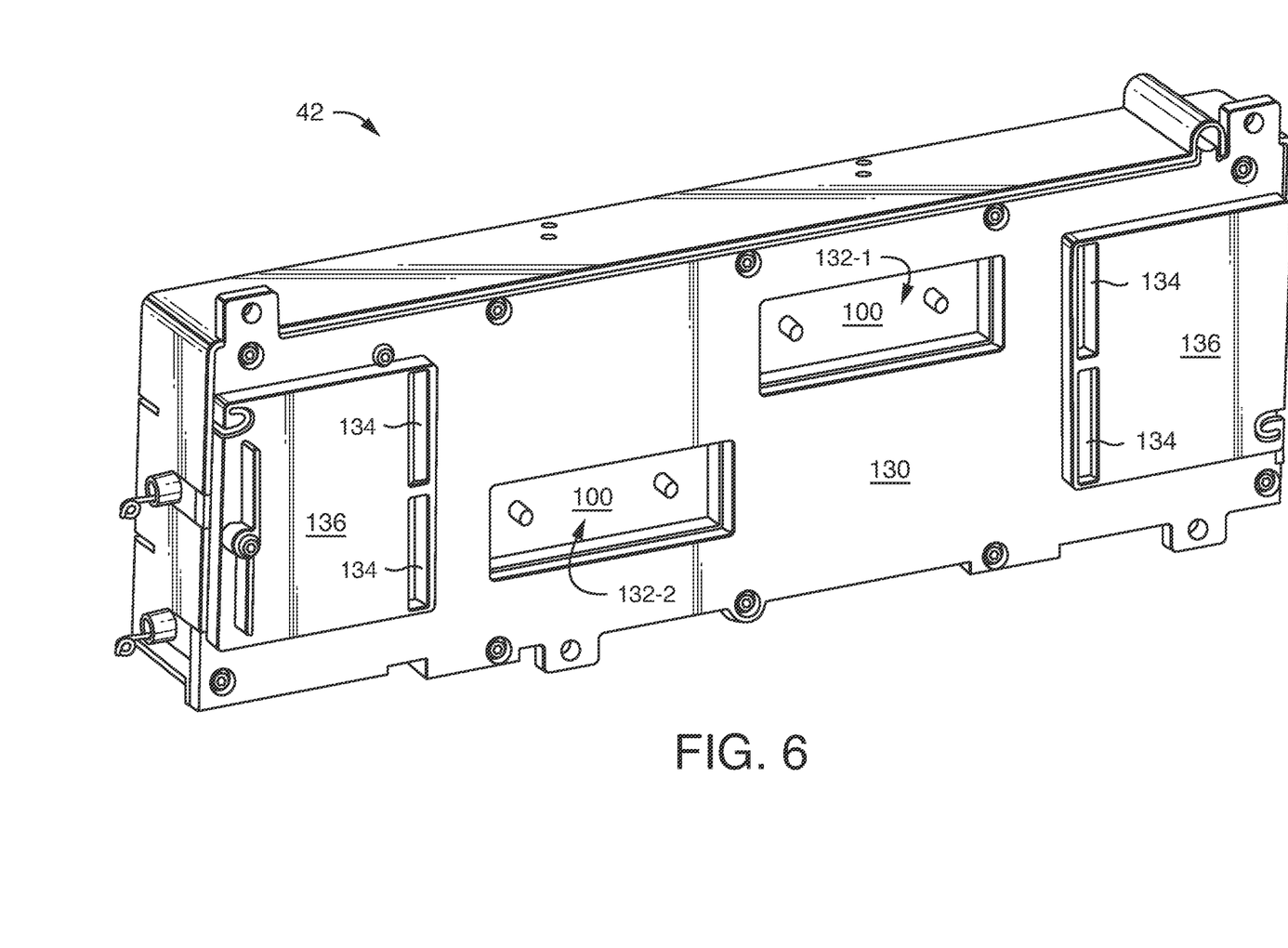
FIG. 6 is a rear view of the column module with its back panel attached, showing windows within which to plug thermal bridges that couple the compartments of the column module to thermoelectric chips that thermally condition the compartments.

FIG. 6 shows the rear view of the column module 42 with its back panel 130. The back panel 130 has two major apertures 132-1, 132-2 (generally, 132). The two major apertures 132 are catty-cornered, each providing a window to the reverse side of the exposed back surface 100 of a different trough, and exposing a contact region on that trough to which a thermal bridge can be physically connected. Alternatively, the major apertures 132 can be catty-cornered along the opposite diagonal, with the major aperture 132-1 providing a window to the lower compartment 72-2 and the major aperture 132-2 providing a window to the upper compartment 72-1. Covers 136 on the back panel 130 cover and protect the pre-heater sockets 78 (FIG. 5) and the ribbon cables 90 (FIG. 3) connected to the pre-heater sockets. Each cover 136 has a pair of minor apertures 134, each sized to permit passage of a ribbon cable 90.

Figure 7:
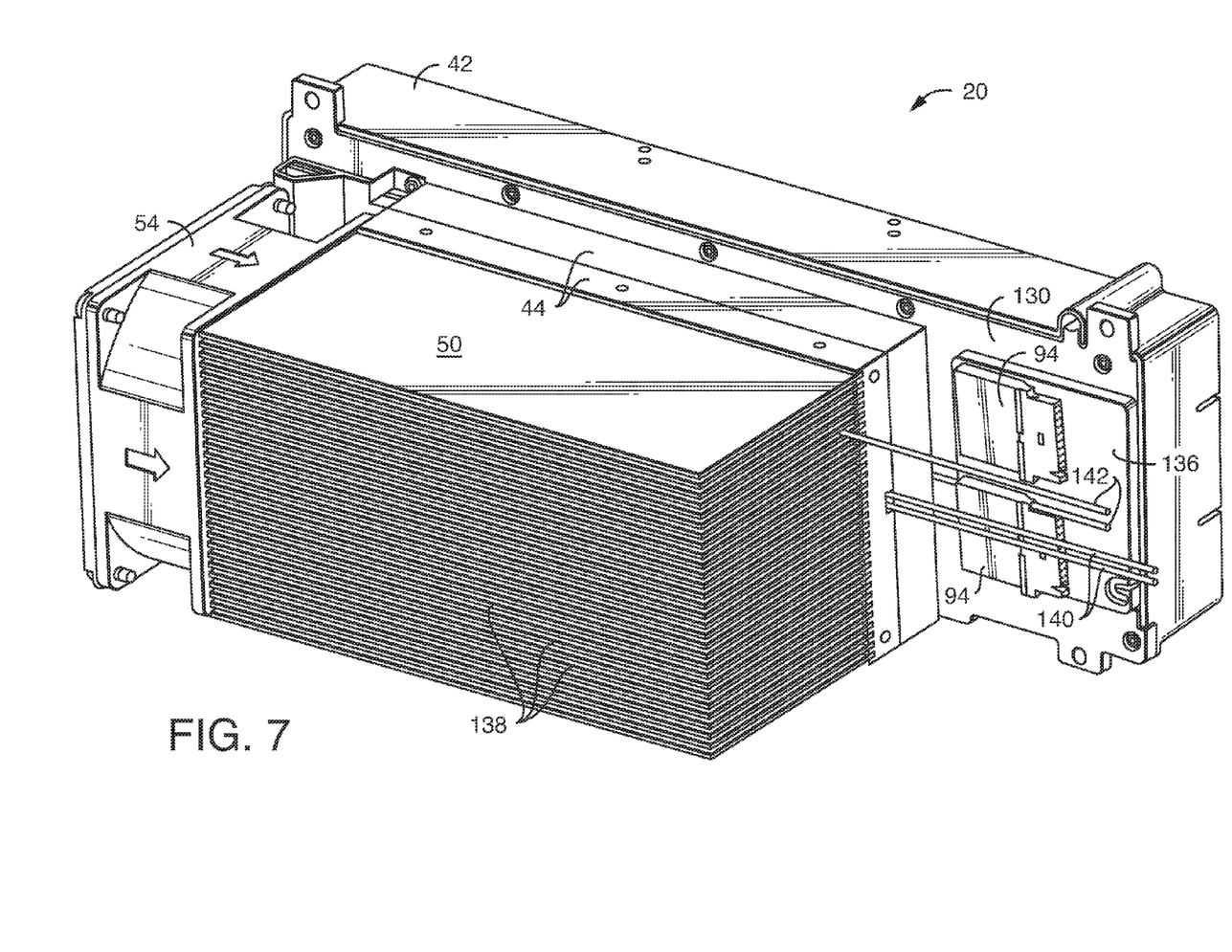
FIG. 7 is a rear view of the column manager, showing a heatsink and a fan.
Figure 9:
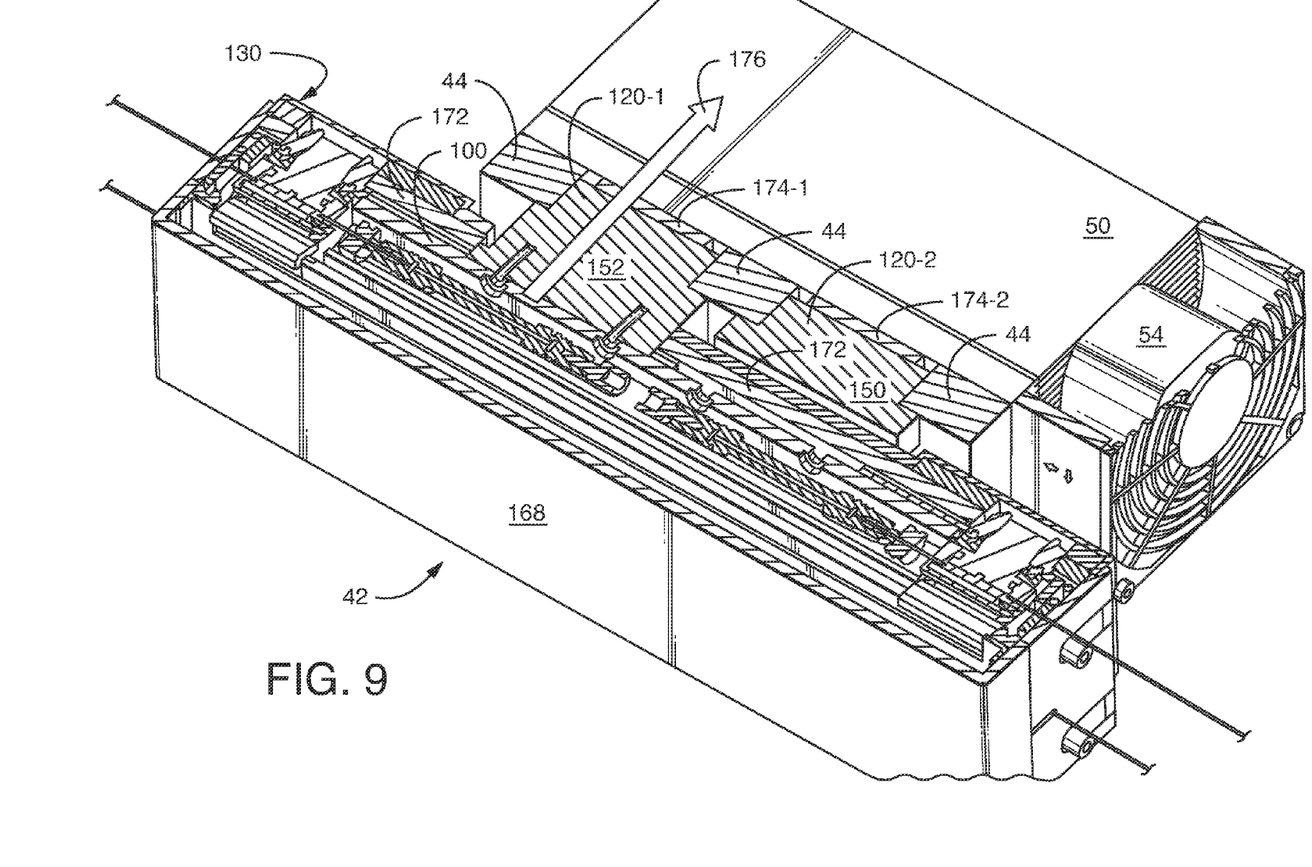
FIG. 9 is a cross-sectional top view of the column manager taken along the line AA' in FIG. 2.

FIG. 7 shows a rear view of the thermal system 20 including the fan 54 coupled to the heatsink 50 comprised of a plurality of thermally conductive spatially separated horizontal blades 138. The heatsink 50 is coupled to the back panel 130 of the column module 42. Disposed between the heatsink 50 and the back panel 130 is the insulation 44 surrounding the thermal bridges (FIG. 8) and thermoelectric chips (FIG. 9). Electrical signal conductors 140 pass through the side of the insulation 44 to convey signals to one of the thermoelectric chips. Although shown to extend through the side of the insulation 44, the electrical signal conductors 140 can pass through the top or the bottom. Depending upon the signals carried by these wires, the thermoelectric chip can be individually controlled to transfer heat to or from the column module 42 (i.e., to heat or to cool). Other electrical signal conductors 142 are electrically connected to a temperature sensor (not shown) embedded in a thermal bridge as shown in connection with FIG. 8. Electrical connectors 94 extend along the surface cover 136. Each of these electrical connectors 94 is connected by a ribbon cable 90 (FIG. 3) that passes through a minor aperture 134 (FIG. 6) and couples to a pre-heater socket 78 (FIG. 5).

FIG. 8 shows a front view of the thermal system 20 with the column module 42 removed to show the thermal bridges 120-1, 120-2 (generally, 120) in more detail. The thermal bridges 120 are made of material with high-thermal conductivity, for example, aluminum. Each thermal bridge 120 has a thin portion 150 and a thick portion 152. The thin portion 150 has a cutout region 154 sized and shaped to receive a temperature sensor 156 (e.g., a thermostat) and the electrical signal conductors 142 connected to the temperature sensor 156. This temperature sensor 156 is part of the electric circuit that drives the thermoelectric chip coupled to that thermal bridge. In the event the temperature sensor measures an excessive temperature, the corresponding thermoelectric chip is turned off. Another temperature sensor (not shown) in the circuit of both thermoelectric chips resides externally coupled to the heatsink 50. In the event this temperature sensor measures an excessive temperature at the heatsink 50, for example, because the fan malfunctions, both thermoelectric chips are turned off.

The thermal bridges 120-1, 120-2 are identical to each other in size and shape, and inverted with respect to each other when mounted to the heatsink 50. The inverted positions enable the thick portion 152 of one thermal bridge 120 to couple physically to one trough (through one major aperture 132 of FIG. 6), while the thick portion 152 of the other thermal bridge physically couples to the other trough (through the other major aperture 132 of FIG. 6). The thick portion 152 also has a pair of threaded holes 158 for receiving fasteners that physically join that thermal bridge 120 to a trough of the column module 42, and bring them into thermally conductive communication. Such fasteners pass through two of the holes 104 (FIG. 3) in the back portion 100 (FIG. 3) of the trough to which that thermal bridge attaches.

In addition, fasteners 160 secure each thermal bridge 120 at its four corners to a thermally conductive side panel 162 of the heatsink 50 and plugged into the back of the column module 42. Sandwiched between each thermal bridge 120 and the side panel 162 is a thermoelectric chip (FIG. 9), each thermal bridge being in thermal communication with a thermoelectric chip, and each thermoelectric chip being in thermal communication with the thermally conductive side panel 162 of the heatsink 50. Electrical signal conductors 140 carry electrical signals to the thermoelectric chips, which are not visible in FIG. 8, being embedded within the insulation 44.

FIG. 9 is a top view taken along the cross section AA' in FIG. 2 (here, the column module 42 has an attached front panel 168). A layer of insulation 172 within the column module 42 is disposed between the troughs 74 and the back panel 130 of the column module 42. Openings in the insulation 172 permit the thermal bridges 120 to directly contact exposed sections of the back surface 100 of the troughs 74.

This cross-section shows one of the thermal bridges 120-1 (i.e., its thick portion 152) coming into direct physical and thermally conductive contact with the back surface 100 of the upper trough 74-1. The thin portion 150 of the other thermal bridge 120-2 does not reach the upper trough 74-1, there being a gap between the back panel 130 of the column module 42 and the thin portion 150. In addition, the thermal bridge 120-1 physically abuts the thermoelectric chip 174-1, which is sandwiched between the thermal bridge 120-1 and the heatsink 50. This thermoelectric chip 174-1 is in direct physical contact with the side panel 162 (FIG. 8) of the heatsink 50. Accordingly, the thermal bridge 120-1 provides a thermal path by which heat can transfer from the trough 74-1 to the heatsink 50 through the thermoelectric chip 174-1, as represented by arrow 176.

Figure 10:
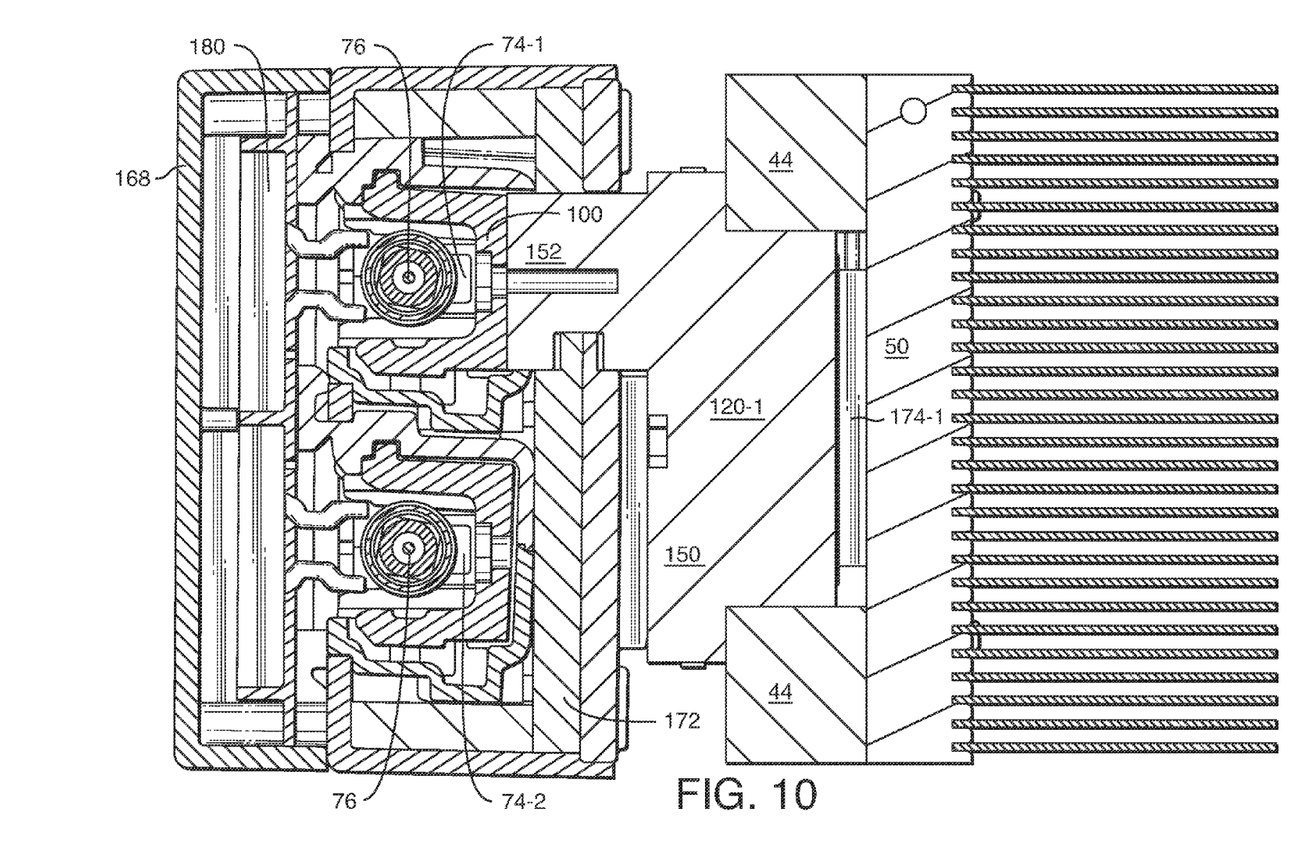
FIG. 10 is a cross-sectional side view of the column manager taken along the line BB' in FIG. 2.

Operation of the other thermoelectric chip 174-2 has minimal affect the temperature of the upper trough 74-1, there being no thermal bridge between the thermoelectric chip 174-2 and the upper trough 74-1. In addition, because of the inverse mounting of the thermal bridges, the thermal bridge 174-2 provides a thermal path by which heat can transfer from the lower trough 74-2 (not shown) to the heatsink 50 through the thermoelectric chip 174-2. Operation of the other thermoelectric chip 174-1 does not affect the temperature of the lower trough 74-2, there being no thermal bridge between the thermoelectric chip 174-1 and the lower trough 74-2. FIG. 10 is a side view taken along the cross section BB' in FIG. 2 (here, again, the column module 42 has an attached front panel 168). The front panel 168 has insulation 180 that urges against the faces of the upper and lower compartments 72-1, 72-2, respectively, thus enclosing those columns 76 installed within the troughs 74-1, 74-2 within an independently controlled thermal environment. This cross-section shows the thick portion 152 of the thermal bridge 120-1 in direct physical and thermally conductive contact with the back surface 100 of the upper trough 74-1. In contrast, the thin portion 150 of the thermal bridge 120-1 is spatially separated from the back panel 130 and does not touch the lower trough 74-2. Further, the insulation layer 172 comes between the lower trough 74-2 and the thin portion 150 of the thermal bridge 120-1, thereby resisting any transfer of heat between them. Accordingly, the thermal bridge 120-1 provides a path by which heat may be exchanged between the trough 74-1 and the heatsink 50 through the thermoelectric chip 174-1, without affecting the temperature of the lower trough 74-2.

The heat transfer achieved by the other thermal bridge 120-2 (FIG. 9) is similar to that achieved by the thermal bridge 120-1, except that the thick portion 152 of the other thermal bridge 120-2, being positionally inverted with respect to the thermal bridge 120-1, comes into physical and thermally conductive contact with the lower trough 74-2, while its thin portion 150 remains spatially separated from the back panel 130 and does not touch the upper trough 74-1. Consequently, the thermal bridge 120-2 operates to conduct heat to the heatsink 50 by virtue of the other thermoelectric chip 174-2 (FIG. 9), without affecting the temperature of the upper trough 74-1.

While the invention has been shown and described with reference to specific preferred embodiments, it should be understood by those skilled in the art that various changes in form and detail may be made therein without departing from the spirit and scope of the invention as defined by the following claims.

What is claimed is:

1. A thermal system for use in a column manager of a liquid chromatography system, comprising:
    a plurality of spatially separated individually controlled thermoelectric chips;
    a column module housing a plurality of thermally conductive troughs, each trough residing in a separate thermal zone to be thermally conditioned individually by one of the individually controlled thermoelectric chips, each trough being adapted to hold one or more liquid chromatography columns therein; and
    a plurality of spatially separated thermal bridges, a first thermal bridge of the plurality of thermal bridges thermally coupling one of the thermoelectric chips to a first one of the plurality of troughs, and a second thermal bridge of the plurality of thermal bridges thermally coupling another of the thermoelectric chips to a second one of the plurality of troughs; and
    the first thermal bridge having a substantially similar shape and size as the second thermal bridge being physically connected to the column module in an inverse position with respect to the second thermal bridge.

2. The thermal system of claim 1, further comprising:
    a heatsink thermally coupled to and shared by the plurality of spatially separated individually controlled thermoelectric chips; and
    a fan coupled to the heatsink, moving air over the heatsink.

3. The thermal system of claim 1, further comprising insulation disposed between neighboring thermoelectric chips to thermally isolate each thermoelectric chip from each neighboring thermoelectric chip.

4. The thermal system of claim 3, wherein a direction of thermal isolation of the thermoelectric chips is orthogonal to a direction of thermal isolation of the thermal zones.

5. The thermal system of claim 1, wherein each thermoelectric chip is capable of individually thermally conditioning the trough to which that thermoelectric chip is thermally coupled to a temperature in a range of approximately 4 to 90 degrees Centigrade.

6. The thermal system of claim 1, further comprising a pre-column solvent heater disposed adjacent to one end of each trough.

7. The thermal system of claim 1, wherein each trough is surrounded on three sides by its own outer shell for capturing moisture, the outer shell having a drain for channeling captured moisture out of the column module.

8. The thermal system of claim 7, wherein each outer shell has a plurality of apertures that exposes sections of the trough surrounded by the outer shell, each exposed section of each trough providing a contact region to which a given thermal bridge may physically and thermally couple; and wherein the column module has a panel that covers all but one exposed section of each trough.

9. The thermal system of claim 1, further comprising a thermostat thermally coupled to one of the thermal bridges and included in an electrical circuit of the thermoelectric chip coupled to that thermal bridge.

10. A liquid chromatography system, comprising:
a column manager receiving a solvent composition to be delivered to a liquid chromatography column, the column manager including a thermal system providing a multi-zone thermal environment for a plurality of liquid chromatography columns, the thermal system comprising:
a plurality of spatially separated individually controlled thermoelectric chips;
a column module housing a plurality of thermally conductive troughs, each trough residing in a separate thermal zone to be thermally conditioned individually by one of the individually controlled thermoelectric chips, each trough being adapted to hold one or more liquid chromatography columns therein; and
a plurality of spatially separated thermal bridges, a first thermal bridge of the plurality of thermal bridges thermally coupling one of the thermoelectric chips to a first one of the plurality of troughs, and a second thermal bridge of the plurality of thermal bridges thermally coupling another of the thermoelectric chips to a second one of the plurality of troughs; and
the first thermal bridge having a substantially similar shape and size as the second thermal bridge being physically connected to the column module in an inverse position with respect to the second thermal bridge.

11. The liquid chromatography system of claim 10, wherein the thermal system further comprises:
a heatsink thermally coupled to and shared by the plurality of spatially separated individually controlled thermoelectric chips; and
a fan coupled to the heatsink, moving air over the heatsink.

12. The liquid chromatography system of claim 10, wherein the thermal system further comprises insulation disposed between neighboring thermoelectric chips to thermally isolate each thermoelectric chip from each neighboring thermoelectric chip.

13. The liquid chromatography system of claim 12, wherein a direction of thermal isolation of the thermoelectric chips is orthogonal to a direction of thermal isolation of the thermal zones.

14. The liquid chromatography system of claim 10, wherein each thermoelectric chip is capable of individually thermally conditioning the trough to which that thermoelectric chip is coupled to a temperature in a range of approximately 10 to 90 degrees Centigrade.

15. The liquid chromatography system of claim 10, wherein the thermal system further comprises a pre-column solvent heater disposed adjacent to one end of each trough.

16. The liquid chromatography system of claim 10, wherein each trough is surrounded on three sides by its own outer shell for capturing moisture, the outer shell having a drain for channeling captured moisture out of the column module.

17. The liquid chromatography system of claim 16, wherein each outer shell has a plurality of apertures that exposes sections of the trough surrounded by the outer shell, each exposed section of each trough providing a contact region to which a given thermal bridge may physically and thermally couple; and wherein the column module has a panel that covers all but one exposed section of each trough.

18. The liquid chromatography system of claim 10, wherein the thermal system further comprises a thermostat thermally coupled to one of the thermal bridges and included in an electrical circuit of the thermoelectric chip coupled to that thermal bridge.

19. The liquid chromatography system of claim 10, further comprising insulation disposed between neighboring thermoelectric chips.

20. A thermal system for use in a column manager of a liquid chromatography system, comprising:
a plurality of spatially separated individually controlled thermoelectric chips;
a column module housing a plurality of thermally conductive troughs, each trough residing in a separate thermal zone to be thermally conditioned individually by one of the individually controlled thermoelectric chips, each trough being adapted to hold one or more liquid chromatography columns therein; and
a plurality of spatially separated thermal bridges, a first thermal bridge of the plurality of thermal bridges thermally coupling one of the thermoelectric chips to a first one of the plurality of troughs, and a second thermal bridge of the plurality of thermal bridges thermally coupling another of the thermoelectric chips to a second one of the plurality of troughs;
wherein each trough is surrounded on three sides by an outer shell for capturing moisture, the outer shell having a drain for channeling captured moisture out of the column module.

21. A liquid chromatography system, comprising:
a column manager receiving a solvent composition to be delivered to a liquid chromatography column, the column manager including a thermal system providing a multi-zone thermal environment for a plurality of liquid chromatography columns, the thermal system comprising:
a plurality of spatially separated individually controlled thermoelectric chips;
a column module housing a plurality of thermally conductive troughs, each trough residing in a separate thermal zone to be thermally conditioned individually by one of the individually controlled thermoelectric chips, each trough being adapted to hold one or more liquid chromatography columns therein; and a plurality of spatially separated thermal bridges, a first thermal bridge of the plurality of thermal bridges thermally coupling one of the thermoelectric chips to a first one of the plurality of troughs, and a second thermal bridge of the plurality of thermal bridges thermally coupling another of the thermoelectric chips to a second one of the plurality of troughs;

wherein each trough is surrounded on three sides by an outer shell for capturing moisture, the outer shell having a drain for channeling captured moisture out of the column module.

* * * * *

UNITED STATES PATENT AND TRADEMARK OFFICE
CERTIFICATE OF CORRECTION

PATENT NO.        : 9,546,986 B2
APPLICATION NO.   : 14/232681
DATED             : January 17, 2017
INVENTOR(S)       : Joshua A. Shreve et al.

It is certified that error appears in the above-identified patent and that said Letters Patent is hereby corrected as shown below:

In the Specification

Column 7, Line 67:
• Begin a new paragraph at "FIG. 10 is a side view..."

Column 8, Line 7:
• Begin a new paragraph at "This cross-section shows..."

Signed and Sealed this
Ninth Day of May, 2017

Michelle K. Lee
*Director of the United States Patent and Trademark Office*